United States Patent [19]

Alzner

[11] Patent Number: 4,919,826
[45] Date of Patent: Apr. 24, 1990

[54] PROCESS AND APPARATUS FOR SEPARATING SOLIDS AND LIQUIDS FROM AN EFFLUENT STREAM

[75] Inventor: Edgar Alzner, Garden City, N.Y.

[73] Assignee: Air Techniques, Incorporated, Hicksville, N.Y.

[21] Appl. No.: 287,987

[22] Filed: Dec. 20, 1988

[51] Int. Cl.[5] ............... A61C 17/04; B01B 49/12; B01D 21/00

[52] U.S. Cl. ............... 210/788; 55/52; 55/192; 210/115; 210/188; 210/195.1; 210/294; 210/537; 210/790; 210/805; 433/92

[58] Field of Search ............... 4/262, 263; 210/104, 210/188, 195.1, 115, 125, 294, 304, 319, 312, 513, 788, 804, 533, 537, 790, 805; 433/92, 97; 417/168, 68, 69; 55/52, 192, 204

[56] References Cited

U.S. PATENT DOCUMENTS

| | | | |
|---|---|---|---|
| 2,230,405 | 2/1941 | Jennings | 417/68 |
| 3,353,378 | 11/1967 | Kahn | 210/115 |
| 3,771,290 | 11/1973 | Stethem | 210/304 |
| 3,964,112 | 6/1976 | Plowman | 433/97 |
| 4,040,961 | 8/1977 | Davis, Jr. et al. | 210/195.1 |
| 4,245,989 | 1/1981 | Folkenroth et al. | 433/92 |
| 4,293,300 | 10/1981 | Cattani | 433/92 |
| 4,344,756 | 8/1982 | Folkenroth et al. | 433/92 |
| 4,564,374 | 1/1986 | Hofmann | 210/104 |
| 4,692,101 | 9/1987 | Fink et al. | 417/68 |
| 4,842,478 | 6/1989 | Durr et al. | 433/92 |

FOREIGN PATENT DOCUMENTS 8603669 7/1986 PCT Int'l Appl. .............. 433/92

*Primary Examiner*—Frank Spear
*Assistant Examiner*—Joseph Drodge
*Attorney, Agent, or Firm*—Louis E. Marn

[57] ABSTRACT

There is disclosed an improved liquid-solids-gas separator assembly permitting recovery of a major portion of the liquid stream for recirculation to a vacuum producing assembly wherein the separator assembly includes a gas-liquid and solids separator chamber and a liquids separator chamber for recovery of a recycle water stream and wherein the separator assembly comprises a vessel defining a cylindrically-shaped chamber into which a dental effluent including water, gases and lighter and heavier than water particles and from which a gas is vented through an upper conduit and liquid streams are recovered from a liquid pool wherein one liquid stream includes lighter than water particles and in one aspect is combined with heavier than water particles and a second liquid stream is recovered for recycling purposes.

11 Claims, 1 Drawing Sheet

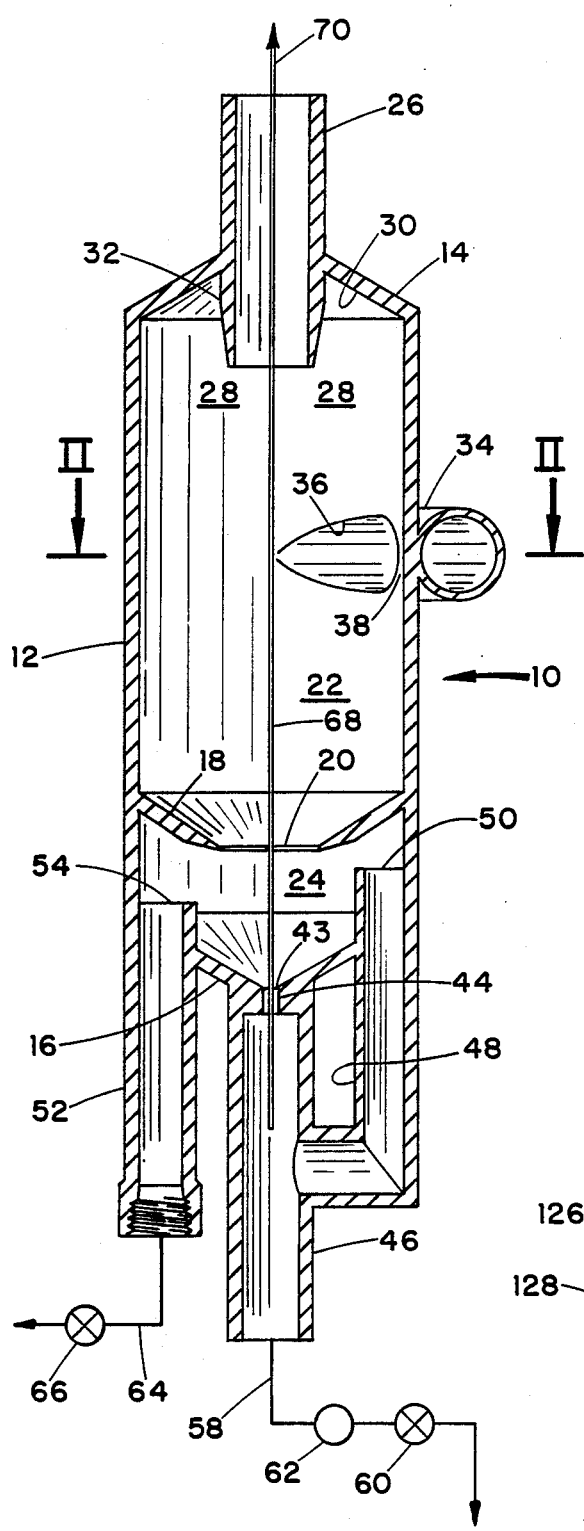
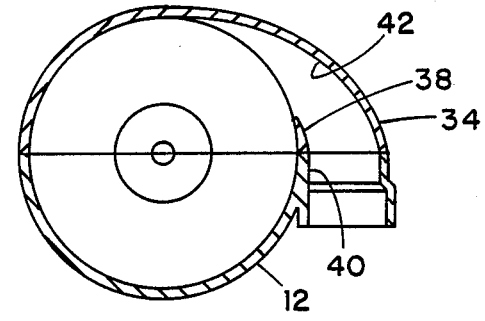
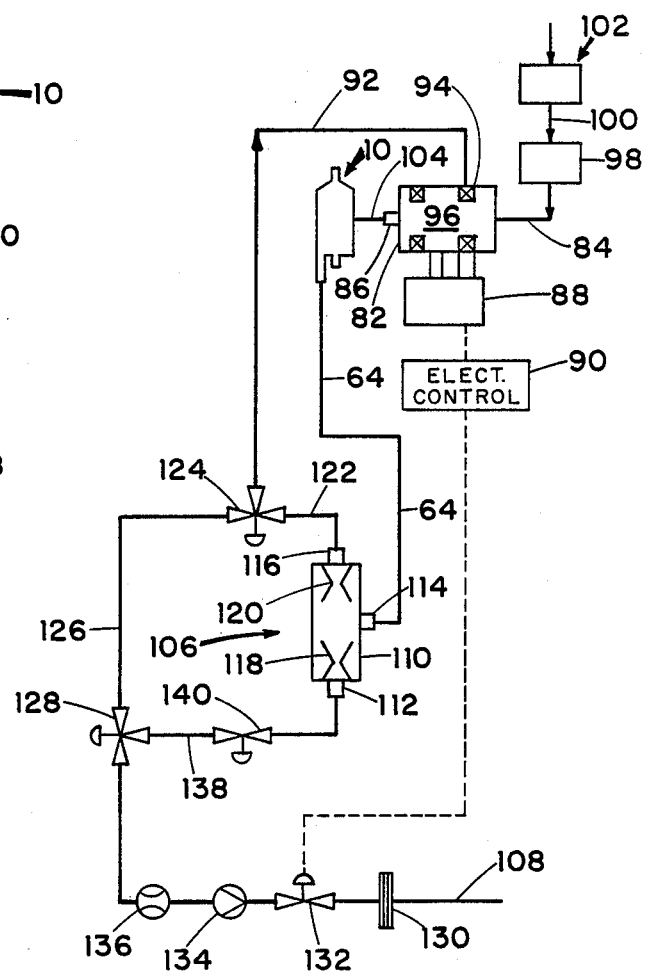
Fig.1
Fig.2
Fig.3

PROCESS AND APPARATUS FOR SEPARATING SOLIDS AND LIQUIDS FROM AN EFFLUENT STREAM

BACKGROUND OF THE INvENTION (1) Field of the Invention

This invention relates to an improved process and apparatus for treating a gas-liquid-solid effluent stream, and more particularly to an improved process and apparatus for separating into component streams a gas-liquid-solids effluent stream resulting from dental procedures.

(2) Description of the Prior Art

A typical dental effluent stream, i.e. from an oral vacuum tube in a dental application contains water, air and other gases, such as nitrous oxide; lighter than water particles, such as human tissue and heavier than water particles, such as ground tooth particles, filling, etc. Most of such particles, and in particular the larger ones, are separated by a screen and filter bowl assembly at the inlet of a pump, such as a water ring vacuum pump. The smaller particles, water, liquids and gases are drawn into the suction side of the vacuum pump and thereafter discharged from the pump. The effluent liquid and gases may be dumped into a vented drain, or as is more prevalent, primarily because of environment codes, are introduced into an air-water separator to separate liquid from gas, dumping the liquid and smaller suspended lighter and heavier than water particles through a trap into a drain and venting to atmosphere the gases via a separate line. The separation of gas-liquid mixtures is not very effective in present dental applications, and significant liquid including contaminants suspended and dissolved in the liquid may be carried away in the vent stream.

Vacuum evacuation systems, for example, used in some dental or process applications, include vacuum pump assemblies having water rings as the prime mover for creation of vacuum. Such pumps must continuously be supplied with water to lubricate and cool internal seals and provide the "piston" action to alternately draw in and expel the liquid-gas mixture designed to be handled by the water rings of such system.

Additionally, and primarily because of environmental, specifically water conservation, reasons, but also for economic and financial reasons, such water based evacuation systems have recently been equipped with water conservation subsystems, commonly referred to as "water recyclers" or "water recirculators". The useful effect, that of recirculating water in such conservation subsystems, is carried out by extracting from the discharged effluent water stream a portion of that waste water flow and re-introducing this portion of recirculated water into the vacuum pump along with a reduced amount of fresh water flow. The net savings of fresh water is the difference between the water consumption without recirculation and that with recirculation. The recirculated water added to the reduced fresh water flow may or may not add up to an amount equal to 100% of the flow normally introduced into the pump when operating without recirculation.

It is assumed that the state of the art and general operation of the water pump is well understood. However, it is important to emphasize the effects of certain parameters on pump performance. These effects/parameters include, but are not limited to, the following, in order of strongest dependence wherein pump's operating efficiency is a function of:

1. the pump supply water temperature;
2. the total quantity of water introduced into the pump;
3. the location in the pump where water is introduced; and
4. the cleanliness of the supply water.

Reasons for such importance, and the explanations for these behaviors are:

1. For a given water inflow rate, a pump can handle a certain volumetric rate of gases. With increasing temperature the vapor pressure of water increases thereby increasing the proportion of water vapor contained in the gas mixture which the pump has to move. Therefore, the volume of gases other than water vapor, namely those entering a dentist's handpiece and/or saliva ejector, and which is the volume of gases desired to be moved by the pump, decreases.

2. At a given water temperature, the performance of the pump increases with increasing quantity of water up to some maximum performance for a specific value of water inflow rate. Above that specific water inflow rate, the pump's performance decreases. This is due to the fact that initially, with small water injection rates, a circular ring of water is built up within a cylindrical cavity and the eccentrically mounted impeller outer radius is only partially immersed in the "water ring". As a greater water rate is added, this outer water ring increases in thickness until the impeller outer radius is continuously in contact with the ring of water. It is for this water ring thickness and the corresponding water injection rate that the pump has maximum performance. By injecting more water, the water ring thickens and the gas moving cavities in the impeller decrease in volume, thereby reducing the volumetric rate of gases that can be moved by the pump.

3. Some water ring pumps introduce the water through the intake manifold, others through special water injection ports built into the pump housing and others use a combination of both. The best performance can be achieved by introducing all of the water through the special injection ports in the housing. This is because bringing the water in through the intake manifold reduces the volume of gas that can occupy the inflow area, and increases the drag on the gases desired to be moved, because the added water must be accelerated by the gas flow. Also, the water in the inlet manifold is broken into droplets, increasing the surface area of the water allowing more water to vaporize thereby decreasing the volume of other gases and ergo decreasing the performance of the pump. This situation is exacerbated during the recirculation of water, because recirculated water is by its very nature warmer, and so a compound degradation of performance results.

4. The cleaner the supply water is, the longer the pump will last and the better it will operate. Dirty injection water will cause abrasion of some pump and ducting parts and coating with biological material on others. Abrasion wears parts, thereby increasing critical tolerances between moving parts which decreases performance. Coating of other parts reduces the volumes and areas which increase flow resistance and decrease flow rates, thereby decreased performance. It is therefore important to extract recirculated water in as clean a state as possible.

In existing water recycling systems, the location of recirculated water extraction is typically within a standard sized or an enlarged version of a common plumbing trap of the drainage stream below an "air-water" separator, regardless of the simplicity or sophistication of such an air-water separator. ("Air" in this context refers to any and all gases in the effluent stream including water vapor.) Such traps contain highly agitated and mixed water flows, and in some applications can easily be "blown out" because of an inefficient upstream air water separator. This provides dirty and at times no recirculation flow, but only gas. This sometimes non-existent or otherwise dirty water is typically introduced into some portion of the intake manifold of the vacuum pump.

OBJECTS OF THE INVENTION

An object of the present invention is to provide an improved process and apparatus for separating into component streams a combined gas-solid-liquid effluent.

Another object of the present invention is to provide an improved process and apparatus for separating into component streams a combined gas-solid-liquid effluent obtained during dental procedure.

Still another object of the present invention is to provide an improved process and apparatus for separating into component streams a combined gas-solid-liquid effluent for recovery of a water stream permitting of its reuse.

A further object of the present invention is to provide an improved process and apparatus for separating into component streams a combined gas-solid-liquid effluent for recovery of a water stream for reuse from which some heavier than liquid particles and some lighter than liquid particles have been removed.

A still further object of the present invention is to provide an improved process and apparatus for separating which provides effluent low level drain for heavier than liquid particles.

Yet another object of the present invention is to provide an improved process and apparatus which allows extraction of relatively cleaner water for another process, and a high level overflow drain for lighter than liquid particles and the balance of liquid to be discharged to another process or waste.

Still another object of the present invention is to provide an improved process and apparatus which allows the centrifugal/gravity separation as an amalgam extractor.

SUMMARY OF THE INVENTION

These and other objects of the present invention are achieved in an improved liquid-solids-gas separator assembly permitting recovery of a major portion of the liquid stream for recirculation to a vacuum producing assembly wherein the separator assembly includes a gas-liquid and solids separator chamber and a liquids separator chamber for recovery of a recycle water stream.

BRIEF DESCRIPTION OF THE DRAWING

Further objects and advantages of the present invention will become apparent upon consideration of the detailed disclosure thereof, especially when taken with the accompanying drawings wherein;

FIG. 1 is a cross-sectional elevational view of the separator assembly;

FIG. 2 is a cross-sectional view taken along the lines II—II of FIG. 1; and

FIG. 3 is a partial schematic flow diagram of a vacuum pump assembly including separator assembly of FIG. 1 and eductor-check valve with by-pass loop assembly.

DETAILED DESCRIPTION OF THE INVENTION

Referring now to the drawings, and in particular FIGS. 1 and 2, there is illustrated a separator assembly, generally indicated as 10 comprised of a generally cylindrically-shaped outer wall 12, a conically-shaped top wall 14, a conically-shaped bottom wall 16 and a conically-shaped intermediate wall member 18 including an opening 20 defining an upper separation chamber 22. The top wall 14 is formed with a vertically-disposed conduit member 26 extending therethrough and into the chamber 22 defining a gas-liquid separation zone 28 defined by an inner surface portion 30 of the top wall 14 with an outer cylindrically-shaped surface portion 32 of the conduit member 26. Extension of the conduit member 26 defined by the surface portion 32 may be omitted depending on the proportions and relationships of surfaces and dimensions of the separator assembly 10.

In a mid portion of the outer wall 12, there is provided a horizontally-disposed inlet conduit member 34 leading to an opening 36 in the outer wall 12. A portion 38 of the outer wall 12, referring to FIG. 2, extends beyond an end portion 40 of the conduit member 34 to direct fluid flow against interior surface portion 42 of the conduit member 34 and inner surface of the outer wall 12 thereby to enhance liquid contact with such interior surface and concomitant gas-liquid separation about such surface portion 42. The frusto-conically-shaped intermediate wall member 18 extends inwardly and downwardly from the outer wall 12. The intermediate wall member 18 is generally parallelly disposed with respect to the bottom wall 16 defining a liquid-liquid-solids lower separation chamber 24. The bottom wall member 16 is formed with a centrally-disposed opening 43 in communication via a channel 44 with a lower vertically-disposed conduit 46 to allow a predetermined amount of liquid and the heavier than liquid particles to drain through the channel 44.

Extending upwardly into the lower separation chamber 24, there are provided a vertically-disposed first conduit member 48 having an upper opening 50 and a second vertically-disposed conduit member 52 having an upper opening 54. The opening 50 and 54 of the first and second conduit members 48 and 52, respectively, are positioned below the intermediate wall member 18 and outside a horizontal area defined by the opening 20, as more fully hereinafter described. It is also the function of member 18 to act as a baffle and fluid diverter to prevent fluid borne debris from droping directly into the openings 50 and 54 upon entering chamber 24.

The opening 50 of the first conduit member 48 is disposed in a horizontal plane above the opening 54 of the second conduit member 52 with the opening 50 of the first conduit member 48 functioning as a weir for overflow of liquids and lighter than liquid particles and the opening 54 of the second conduit member 52 functioning to allow extraction of liquids from which significantly heavier and lighter than liquid particles have been removed. The conduit member 48 is in fluid communication via an opening 56 with the lower conduit member 46 which is in fluid flow communication by line 58 through a plumbing trap 60 to a disposal system (not shown). Alternately, conduits 48 and 46 may be configured to not join at opening 56, thereby allowing liquid with predominantly lighter than water particles and liquid with predominantly heavier than liquid particles to be drained separately. Such separate draining, for example could enhance the separation of small amalgam particles from the disposal system.

The second conduit member 52 is in fluid flow communication by line 64 under the control of valve 66 with the vacuum pump assembly, as more fully hereinafter described. vertically-disposed and extending downwardly through the opening 43, there is provided an agitating wire member 68 mounted (not shown) for lateral and/or rotational movement within the channel 44 to prevent solids build-up about the opening 43 and within channel 44. The conduit member 26 is in gaseous communication in the direction of line 70 with the atmosphere.

The separator assembly 10 of the present invention is included in another aspect of the present invention to provide a portion of the water requirement for the water rings of the prime mover of a vacuum pump assembly for creation of vacuum, generally indicated as 80, referring now to FIG. 3. The vacuum pump assembly 80 is comprised of a vacuum pump 82 including an inlet conduit 84 and an outlet conduit 86, pump motor 88 and an electrical box 90. The vacuum pump 82 is provided with a water supply line 92 in fluid flow communication with water rings 94 and the housing chamber 96 of the vacuum pump 82 as more fully hereinafter described. The inlet conduit 84 of the vacuum pump 82 is in fluid flow communication with a solid filter assembly 98 which is in fluid flow communication by line 100 with a vacuum valve assembly, generally indicated as 102, such as described in copending U.S. application Ser. No. 193,769, filed May 13, 1988, assigned to the same assignee as the present invention and incorporate herein by reference. The outlet conduit 86 of the vacuum pump 82 is connected by line 104 to the inlet conduit member 34 of the separator assembly 10.

The water supply line 92 is in fluid flow communication with an eductor assembly, generally indicated as 106, with a source of fresh water in line 92 and recirculated water in line 64 as more fully hereinafter described. The eductor assembly 106 includes an eductor housing 110 having a fresh water inlet conduit 112, a recirculation inlet conduit 114 and an outlet conduit 116 and is provided with a nozzle 118 and a venturi device 120. The outlet conduit 116 of the eductor assembly 106 is in fluid flow communication via line 122 under the control of three way valve (or tee and check valve) 124 with the water supply line 92 for the vacuum pump assembly 80. The three way valve 124 is in fluid flow communication by line 126 with the three-way valve 128 as more fully hereinafter described.

The fresh water supply line 108 is in fluid flow communication with the fresh water inlet conduit 112 of the eductor assembly 106 via a strainer 130, a valve assembly 132 under the control of a solenoid (not shown) operated by the electric control assembly 90, one way valve 134, a flow restrictor 136 and thence through three-way valve 128 via line 138 under the control of pressure regulator 140.

In operation referring to FIG. 3, a vacuum stream in line 100 from the vacuum valve assembly 102 including liquids, water, water vapor, gaseous components and solid particulate material including tooth particles, filling materials, decay, etc. is passed by line 100 through the solids filter unit 98 and thence by line 84 to the suction side or inlet of the vacuum pump 82. In the solids filter assembly 98, particulate material having a particular size of greater than about 400 $\mu$ are separated from the stream prior to inhalation of a resulting gas-liquid-solid mixture in line 84 into the vacuum pump 82. Water introduced by line 92 to the water rings 94 and into the chamber 96 is combined with the mixture and passed by line 104 from outlet conduit 86 of the vacuum pump 82 into the separator assembly 10 for processing as more fully hereinafter described, to provide a recirculation water stream in line 64. The liquid stream in line 64 from the separator assembly 10 is passed to the inlet conduit 114 of the eductor assembly 106.

The water requirements for the vacuum pump assembly 82 are provided by fresh water in line 108 and the recirculation water in line 64 with the pressure of the fresh water stream in line 138 providing the means for forming the water stream in line 92 introduced into the vacuum pump 82. The pressure of the fresh water stream in line 108 is generally of from about 30 to about 100 psig. regulated to 30 psig. by pressure regulator 140 and under the control of valve 132 in response to an on-mode condition of the motor 88 is passed through the strainer 130 to remove any particulate material of a particulate size greater than 200 $\mu$, and is thence passed through the flow restrictor 136 to control waterflow rate, generally 0.5 to 0.75 gpm. depending on pump size prior to introduction into the eductor assembly 106 for passage through the nozzle 118 to entrain recirculating water in line 64 introduced by conduit 114 and form a combined water stream in line 122 after passage through the venturi 120, which is preferably of like pressure and of a like quantity of a fresh water stream, per se, which would be necessary to operate the vacuum pump assembly 82 by passage thereto by line 126 under the control valves 128 and 124 and thence through line 92 in the absence of such recirculation water stream, sometimes referred to as the by-pass path.

In such manner, fresh water requirements for the vacuum pump 82 are substantially reduced, e.g. of from 25 to 40 percent of usual fresh water requirements, and thus provides a corresponding savings of from 75 to 60 percent of fresh water as well as concomitantly reducing discharge requirements of an untreated effluent stream withdrawn from the discharge side of the vacuum pump 82. The amount of recirculated water flow will vary slightly depending on operating condition of the system at any given time, but is always sufficient to provide for proper operation of the vacuum pump 82. Generally, fresh water supply is a relatively fixed value depending primarily on the pressure of the fresh water supply and the nozzle orifice size. Should the eductor assembly 106 become inoperative, the fresh water requirements for the vacuum pump assembly 82 in line 92 may be supplied from the fresh water supply line 108 via line 126 under the control of by-pass valves 128 and 124.

It has been found that the pump performance, as measured and judged by both the volume flow rate of ingested gases, such as air at a given vacuum pressure and the highest vacuum pressure attainable, is a function of both the amount of liquid and the temperature of the liquid entering the pump. There is an optimum liquid rate below and above which the performance of a liquid ring pump deteriorates and as the liquid temperature increases the performances decreases, the latter being the stronger influence. Increasing the liquid rate also increases the load on the pump and hence the power requirement. Increasing the temperature of the liquid into the pump decreases the performance of the pump due to the increased vapor pressure of the liquid.

Recirculated liquid has an increased temperature, therefore, mixing recirculated liquid with fresh liquid increases the temperature of the pump supply liquid correspondingly. Based on liquid supply flow rate only, it would seem that the recirculated fluid plus fresh fluid should total the design flow rate for maximum performance. However, because of the stronger dependence of performance on liquid temperature, it is desirable to entrain less than the full amount of recirculated liquid for optimal recirculation performance, which because of temperature reasons is always less than total fresh water injection performance. In any case, the fresh water supply rate in the recycling mode of this manifestation is independent of and unaffected by the variation of recirculated water flow rate, being determined by the regulated liquid supply pressure and the diameter of the nozzle opening in the eductor hereinafter described.

The gas-liquid-solid effluent stream withdrawn from the outlet conduit 86 of the vacuum pump 82 is passed by line 104 to the inlet conduit member 34 of the separator assembly 10, referring now to FIG. 1. The effluent stream is tangentially introduced into the chamber 22 of the separator assembly 10 along inner surface of the wall 12 thereof at force sufficient to permit gas-liquid separation with eventual gas removal via conduit 26 and vented via line 70 to the atmosphere. To insure gas separation from the liquid and solids, the separator assembly 10 is formed with the gas-liquid separation zone 28 whereby any liquid and entrained solids rising up the surface of the wall 12 contacts the outer surface 32 of the conduit member 26 for gravity flow downwardly along the outer surface 32 through the upper chamber 22 into the liquid-solids collection and separator chamber 24. The liquid and entrained solids flow downwardly through the opening 20 in the intermediate plate member 18 and thence into the separator and collection chamber 24 with solids build-up about the base portion of the bottom wall member 16.

In the lower separation chamber 24, the liquid phase is collected under conditions establishing a liquid level (L) as determined by the height of the opening 50 with lighter than liquid particles and lighter liquids permitted to overflow the opening 50 and flow down the conduit 48 to be admixed in conduit 46 with heavier than liquid particulate matter and heavier liquids passing through the channel 44. The agitating member 68 is freely disposed through the orifice 43 and into the channel 44 to minimize solids build-up. The liquid flow rate through orifice 43 and channel 44 is fixed by the diameter of orifice 43 thereby establishing the diameter of agitating member 68 and the head of liquid to the level of opening 50, as understood by one skilled in the art. The combined liquid-solids stream in conduit 46 is withdrawn by line 58 and passed to waste discharge.

By keeping conduits 48 and 46 separate, it is possible to separately discharge lighter and heavier than liquid particles. Intermediate density liquids, primarily water, is withdrawn through the opening 54 and passed by conduit member 52 to line 64 under the control of valve 66 as the recirculation water stream to be passed to the inlet conduit 114 of the eductor assembly 104 as hereinabove discussed.

It is well known that the total energy of a system consists of the sum of kinetic energy, potential energy and thermal energy. In a gas stream, by comparison, the potential energy is negligible and can therefore be ignored. If a gas stream contains kinetic energy of motion and this motion is abruptly and turbulently brought to a significantly smaller velocity, the organized kinetic energy of the gas stream is converted into thermal energy primarily through frictional effects. If another fluid, such as a liquid is intermixed with the gas, this thermal energy is absorbed by the liquid thus raising its temperature. If, on the other hand the liquid is significantly separated from the gas prior to any frictional deceleration, and such deceleration is minimized by proper aerodynamic design, a significant amount of kinetic energy can be transported to be lost in a region remote from where the liquid can absorb that converted heat, then the separated water would have a temperature below that of the abrupt and turbulent deceleration previously described.

The present invention possesses the characteristics of heat dissipation, such that heat is transported away by a highly vortical exiting air stream where the heat is dissipated in the gas vent instead of being transmitted to the fluid within the gas-liquid separation chamber. This is achieved by means of the tangential and smooth surface junctions of surfaces, the introduction of fluids into the separation chamber in a smooth, tangential manner via a slowly varying cross sectional area inlet and the imparting to the gas a high vortical or angular velocity.

The concomitant centrifugal and centripetal forces created by the configuration design separate the fluid very quickly from the gas, then draining peripherally under the action of gravity to expose minimal surface area to the gas for absorption of thermal energy. The turbulent discharge cited as an example of the prior art contains many droplets which in total have a very large surface area and are in the abruptly slowed warmed gas flow, therefore providing an enhanced liquid warming environment. Although this effect is not a major thermal load, it nevertheless underscores another advantage of the embodiment of this invention.

EXAMPLE OF THE INVENTION

Operation of the process and apparatus of the present invention is described in the following example which is intended to be merely illustrative and the invention is not to be regarded as limited thereto.

EXAMPLE

A nominally rated 1.0 horsepower motor drives a water ring vacuum pump capable of evacuating about 900 standard cubic feet per minute of air (and/or gas mixture) at a vacuum pressure of about 5 inches of mercury (and about 700 scfm at about 9 inches of mercury) requiring about one half gallon per minute of water for optimum performance. The eductor is constructed with a nozzle diameter to deliver water with a flow rate of 25% of ½ gpm or about ⅛ gpm and consistent with a regulated fresh water supply pressure of about 30 psig. Low pressure recirculated water is entrained by the fresh water in the eductor for delivery at the intermediate pressure into the regular injection ports of the pump housing. The clean water separator extracts a portion of the 400 μ debris from the recirculated water thereby reducing the total amount of debris which is reintroduced into the vacuum pump, as compared to systems of the prior art. Recirculation in accordance with the present embodiment reduces pump performance by only between 2% and 8% depending on the vacuum and suction flow rate, as compared to the recirculation methods of the prior art which exhibit reductions of from 4% to 16% for similar recirculation water temperature and flow rate. Reducing the amount of fresh water into the pump and recirculating a portion of the total amount of water required by the pump for optional operation also reduces the amount of water discharged as actual waste stream.

Thus, in accordance with the present invention, there is a significant reduction in quantity of a waste stream to enter the local disposal treatment plants. Additionally, there is a significant reduction in fresh water requirements providing economic benefits through reduced fresh water consumption. The system permits facile operation with minimum requirements for operator maintenance and control as well as providing for emergency override fluid by-pass to minimize potential damage and/or downtime to the vacuum pump assembly.

While the present invention has been described with reference to cylindrical and circular shapes, and it is obvious to one skilled in the art that spiral and elliptically shaped surfaces and shapes such as frustum conical surfaces create equivalent boundaries for providing centripetal forces for liquid separation from gases and heavier than liquid particles from liquids. It is also recognized that the aspect ratio of diameter to height of various components can be varied within the context of these separation phenomena. Furthermore it is essential to recognize that the conical member 18 whether implemented as show in FIG. 1, or inverted as alternately described herein earlier, performs the same function of baffling and in the limit could be a flat disk with suitable perforations. The importance of this baffle member is that it acts as a baffle serving both to direct liquid and shield the drainage openings as well as to separate the turbulent and agitated gasflow from the smoother desired liquid discharge flow.

In addition, should a recycling liquid system not be required, the gas-liquid separation device pictured in FIG. 1 can be used strictly as a gas-liquid separator in such a manner that all drainage paths are combined to form one leading into a common plumbing trap for liquid discharge. A simplification of the discharge channels is then possible by eliminating conduits 52 and 48, enlarging orifice 42 and thus duct 44, and eliminating the agitation device 68. The baffle 18 is then an optional component and is not required, except to reduce internal splashing.

The curved inlet duct 34 can also be shaped in such a fashion that the cross sectional flow area increases gradually and smoothly to allow smooth deceleration of the pump discharge flow while simultaneously being curved to provide simultaneous centrifugal separation of the liquid from the gases. Smooth deceleration of the incoming stream allows gravity to contribute to the separation process early on.

The benefits accrued in this embodiment are:
1. a defined and specific reduction in fresh water consumption, 75% in this example;
2. a defined and specific reduction of liquid subject to disposal into the environment, 75% in this example;
3. reduction of debris particulates recirculated through the pump;
4. injection of recirculated and fresh water directly into the pump housing water injection ports;
5. optimization of recirculated water quantity to minimize reduction of performance due to water temperature rise;
6. internal aerodynamic design to preclude blowing out of traps, and to minimize the expulsion of water droplets with the separated air stream.

While the invention has been described in connection with an exemplary embodiment thereof, it will be understood that many modifications will be apparent to those of ordinary skill in the art; and that this application is intended to cover any adaptations of variations thereof. Therefore, it is manifestly intended that this invention be only limited by the claims and equivalents thereof.

What is claimed:

1. An apparatus for separating a multi-component dental stream comprising water, gases, lighter than water particles and heavier than water particles, which comprises:
   a vessel having a side wall, a top wall and a bottom wall defining a cylindrically-shaped chamber;
   a gaseous outlet conduit means extending upwardly from said top wall of such vessel for venting a gas from said chamber;
   an outlet conduit extending from a lower portion of said bottom wall for withdrawing liquid and particles from said chamber;
   an inlet conduit means disposed on said wall for tangentially introducing said multi-component stream into said chamber;
   an intermediate wall member including an orifice disposed in said chamber of said vessel defining a lower liquids separation zone;
   a first and second liquid outlet conduit means extending into said liquid separation zone for withdrawing a respective liquid stream therefrom, said first liquid outlet conduit means having an inlet above an inlet for said second liquid outlet conduit means, said intermediate wall member extending over said inlets to said first and second liquid outlet conduit means;
   a first valve means for controlling flow of said liquid stream including lighter than water particles through said first outlet conduit means; and
   a second valve means for controlling flow of said liquid stream through said second outlet conduit means.

2. An apparatus for separating a multi-component stream as defined in claim 1 and further including an outlet orifice positioned at a lower portion of said liquids separation zone for withdrawing said heavier than water particles.

3. An apparatus for separating a multi-component stream as defined in claim 2 and further including an agitator extending through said outlet orifice to minimize build-up of heavier than water particles.

4. An apparatus for separating a multi-component stream as defined in claim 2 whereas said liquid stream of said first outlet conduit means is combined with said heavier than water particles prior to withdrawal through said outlet conduit.

5. An apparatus for separating a multi-component stream as defined in claim 1 wherein said gaseous outlet conduit means extends into said chamber.

6. An apparatus for separating a multi-component stream as defined in claim 1 and further including a wall portion extending into said inlet conduit means to direct said multi-component stream against said side wall of said chamber.

7. An apparatus for separating a multi-component stream as defined in claim 1 wherein said intermediate wall member is conically-shaped.

8. An apparatus for separating a multi-component stream as defined in claim 1 wherein said valve means are controlled to provide a liquid level in said liquid separation zone at said inlet to said first liquid outlet means.

9. A process for separating a multi-component stream comprising water, gases, lighter than water particles and heavier than water particles, which comprises:
   introducing said multi-component stream into a cylindrically-shaped gas-liquid separation zone to form a gaseous stream and a liquid stream including particles;
   introducing said liquid stream including particles into a liquid-liquid separation zone including a pool of liquid disposed below said gas-liquid separation zone and separated therefrom by an intermediate plate member extending into said zone;
   withdrawing a liquid stream including lighter than water particles overflowing said pool of liquid and shielded by said intermediate plate member;
   withdrawing a liquid stream which is relatively free of particles from an intermediate of said pool of liquid and shielded by said intermediate plate member; withdrawing a liquid stream including heavier than water particles from a lower portion of said pool of liquid; and
   controlling flow of liquid from said liquid-liquid separation zone to establish said pool of liquid.

10. A process for separating a multi-component stream as defined in claim 9 wherein said multicomponent stream is tangentially introduced into said gas-liquid separation zone to facilitate gas-liquid separation.

11. A process for separating a multi-component stream as defined in claim 9 wherein particulates are withdrawn from a lower portion of said liquid-liquid separation zone and combined with said liquid stream overflowing said pool of liquid.

* * * * *